(12) United States Patent
Vidovich

(10) Patent No.: US 11,583,626 B2
(45) Date of Patent: Feb. 21, 2023

(54) MULTI-ANGULATED CATHETER

(71) Applicants: The Board of Trustees of the University of Illinois, Chicago, IL (US); The US Government Represented by the Department of Veterans Affairs, Washington, DC (US)

(72) Inventor: Mladen I. Vidovich, Chicago, IL (US)

(73) Assignees: The Board of Trustees of the University of Illinois, Urbana, IL (US); The US Government Represented by the Department of Veteran Affairs, Washington, DC (US)

( * ) Notice: Subject to any disclaimer, the term of this patent is extended or adjusted under 35 U.S.C. 154(b) by 177 days.

(21) Appl. No.: 16/673,186

(22) Filed: Nov. 4, 2019

(65) Prior Publication Data

US 2020/0061283 A1   Feb. 27, 2020

Related U.S. Application Data

(62) Division of application No. 13/722,511, filed on Dec. 20, 2012, now Pat. No. 10,463,781.
(Continued)

(51) Int. Cl.
*A61M 5/00* (2006.01)
*A61M 25/00* (2006.01)

(52) U.S. Cl.
CPC ........ *A61M 5/007* (2013.01); *A61M 25/0041* (2013.01)

(58) Field of Classification Search
CPC .......................... A61M 5/007; A61M 25/0041
See application file for complete search history.

(56) References Cited

U.S. PATENT DOCUMENTS

| 4,033,331 A | 7/1977 | Guss et al. |
| 4,747,840 A | 5/1988 | Ladika et al. |

(Continued)

FOREIGN PATENT DOCUMENTS

WO   199930762   6/1999

OTHER PUBLICATIONS

Agostoni et al., 'Radial Versus Femoral Approach for Percutaneous Coronary Diagnostic and Interventional Procedures', JACC vol. 44 No. 2, pp. 349-356, 2004.
(Continued)

*Primary Examiner* — Bo Joseph Peng
(74) *Attorney, Agent, or Firm* — Dorsey & Whitney LLP

(57) ABSTRACT

The present invention is directed to a multi-angulated catheter and methods of using the multi-angulated catheter. The multi-angulated catheter is so dimensioned as to facilitate accessing the left ventricle from an arm of a patient. The multi-angulated catheter generally includes in order: (a) a coiled end; (b) a first straight portion having a first straight portion length; (c) a first shaft including a distal end connected to the first straight portion and a proximal end opposite the distal end, the first shaft and the first straight portion defining a first obtuse angle, the first shaft having a first shaft length; and (d) a second shaft connected to the first shaft on said proximal end. The catheter is flexible so as to afford being straightened when it is advanced over a guide wire. The catheter resiliently returns to a multi-angulated position after the guide wire is withdrawn.

18 Claims, 4 Drawing Sheets

Related U.S. Application Data

(60) Provisional application No. 61/705,183, filed on Sep. 25, 2012, provisional application No. 61/578,036, filed on Dec. 20, 2011.

(56) References Cited

U.S. PATENT DOCUMENTS

| | | |
|---|---|---|
| 5,037,403 A | 8/1991 | Garcia |
| 5,203,776 A | 4/1993 | Durfee |
| 5,215,540 A | 6/1993 | Anderhub |
| 5,306,263 A | 4/1994 | Voda |
| 5,403,292 A | 4/1995 | Ju |
| 5,445,625 A | 8/1995 | Voda |
| 6,036,682 A | 3/2000 | Lange |
| 6,277,107 B1 | 8/2001 | Lurie et al. |
| 6,285,903 B1 | 9/2001 | Rosenthal et al. |
| 6,355,026 B1 | 3/2002 | Mick |
| 6,926,669 B1 | 8/2005 | Stewart et al. |
| 7,993,351 B2 | 8/2011 | Worley et al. |
| 2003/0114832 A1 | 6/2003 | Kohler et al. |
| 2005/0273006 A1 | 12/2005 | Stewart et al. |
| 2008/0027334 A1 | 1/2008 | Langston |
| 2009/0082756 A1 | 3/2009 | Vidyarthi |
| 2010/0069820 A1 | 3/2010 | Zotz |

OTHER PUBLICATIONS

Campeau, Catheterization & Cardiovascular Diagnosis 16, pp. 3-7, 1989.
Extended European Search Report dated Jun. 13, 2016 for EP13840954.5.
International Preliminary Report dated Apr. 9, 2015 for PCT/US2013/061301.
International Search Report and Written Opinion dated Dec. 18, 2013 for PCT/US2013/061301.
Notice of Allowance dated Aug. 7, 2019 for U.S. Appl. No. 13/722,511.
Office Action dated Apr. 6, 2016 for U.S. Appl. No. 13/72,511.
Office Action dated May 15, 2017 for U.S. Appl. No. 13/722,511.
Office Action dated Jun. 16, 2015 for U.S. Appl. No. 13/722,511.
Office Action dated Sep. 15, 2016 for U.S. Appl. No. 13/722,511.
Office Action dated Oct. 27, 2017 for U.S. Appl. No. 13/722,511.
Board Decision dated Jul. 1, 2019 for U.S. Appl. No. 13/722,511.

MULTI-ANGULATED CATHETER

CROSS-REFERENCE TO RELATED APPLICATIONS

This application is a divisional of U.S. patent application Ser. No. 13/722,511, filed Dec. 20, 2012, which claims the benefit of priority to U.S. Provisional Patent Application Nos. 61/578,036, filed Dec. 20, 2011, and 61/705,183, filed Sep. 25, 2012, each of which are hereby incorporated by reference in their entireties.

FIELD OF THE INVENTION

This invention relates generally to coronary catheters. More particularly, this invention relates to an improved, preshaped catheter for use in cardiac ventriculography.

BACKGROUND OF THE INVENTION

Cardiac ventriculography is the radiographic examination of a ventricle of the heart that involves injection of an x-ray contrast agent, usually iodinated contrast dye, into the heart's ventricle(s), typically the left ventricle. This iodinated contrast material can be traced through the heart using special cameras or scanners thereby enabling studies of the pumping function of the heart.

However, the left ventricle may be a particularly difficult chamber of the heart to obtain x-ray imaging. Presently, so-called pigtail catheters are used, being threaded retrogradely through the aorta, around the aortic arch, and through the aortic valve until the distal tip of the catheter resides in the ventricle. Then, with the patient under an x-ray machine such as a fluoroscope, a bolus of x-ray contrast fluid is injected through the catheter at a high pressure (500-900 psi) into the ventricle, to quickly fill the ventricle with x-ray contrast media. For a moment, details of the heart structure and action become visible by x-ray imaging, until the contrast media is pumped out of the ventricle.

Pigtail catheters used in cardiac ventriculography are produced by numerous medical supply companies and are available in a range of lengths and sizes to meet different needs. Currently pigtail catheters are designed as either "straight" with no angle or "angled" with angulations of 145 and 155 degrees. However, with the radial approach the angle of the aorta is not favorable for these catheters and they may be more difficult to insert into the left ventricle compared to the femoral approach. Thus, there has developed a need for a catheter that is so dimensioned as to facilitate accessing the left ventricle from an arm of a patient.

SUMMARY OF THE INVENTION

The inventor has discovered that a different angulation design, more particularly from about 105 to 140 degrees and introduction of another angle to the catheter at various distances from the tip makes the standard pigtail catheter more suitable for the radial approach.

Accordingly, in an embodiment, this invention is a multi-angulated catheter comprising, in order: (a) a coiled end; (b) a first straight portion having a straight portion length, (c) a first shaft connected to said first straight portion at a first obtuse angle, wherein said first shaft has a first shaft length, said first shaft including a distal end connected to said first straight portion and a proximal end opposite said distal end, and (d) a second shaft connected to said first shaft on said proximal end, said first shaft extending from said second shaft at a second obtuse angle, one of said first and second obtuse angles being a positive angle and the other being a negative angle. The multi-angulated catheter is flexible so as to afford being straightened when it is advanced over a guide wire. The multi-angulated catheter returns to a multi-angulated position after the guide wire is withdrawn. The first straight portion length, the first shaft length, and the first and second obtuse angles are so dimensioned as to facilitate accessing a left ventricle from an arm of a patient.

In another embodiment, this invention is a multi-angulated catheter comprising in order: (a) a coiled end; (b) a first straight portion having a first straight portion length; (c) a first shaft including a distal end connected to said first straight portion and a proximal end opposite said distal end, said first shaft having a first shaft length; and (d) a second shaft connected to said first shaft on said proximal end. The multi-angulated catheter is flexible so as to afford being straightened when it is advanced over a guide wire. The multi-angulated catheter returns to a multi-angulated position after the guide wire is withdrawn. The first shaft and the first straight portion define a first obtuse angle when viewed from a direction substantially perpendicular to a plane defined by the first and second shaft. The first straight portion extends out of plane with respect to a plane defined by the first and second shafts.

In another embodiment, this invention is a method for radial ventriculography comprising inserting a guide wire into an arm of a patient and inserting a multi-angulated catheter over said guide wire into said arm. The multi-angulated catheter comprises a coiled end, a first straight portion, a first shaft connected to the first straight portion at a first obtuse angle, the first shaft including a distal end connected to the first straight portion and a proximal end opposite the distal end, and a second shaft connected to the first shaft on the proximal end. The multi-angulated catheter is then advanced over the guide wire through an artery into the patient's heart. The multi-angulated catheter is flexible so as to afford being straightened when it is advanced over the guide wire. The guide wire is then withdrawn, whereupon the multi-angulated catheter returns to a multi-angulated position. The multi-angulated catheter is then advanced in the multi-angulated position into a left ventricle of the patient. A radiopaque dye is then injected into the left ventricle, and a visual representation is made of the left ventricle.

Other aspects of the invention will become apparent by consideration of the detailed description and accompanying drawings.

DETAILED DESCRIPTION

Described herein is a multi-angulated catheter and methods of using the multi-angulated catheter for delivering radiopaque media. The multi-angulated catheter is so dimensioned as to facilitate accessing the left ventricle from an arm of a patient. The multi-angulated catheter generally includes in order: (a) a coiled end; (b) a first straight portion having a first straight portion length; (c) a first shaft including a distal end connected to the first straight portion and a proximal end opposite the distal end, the first shaft and the first straight portion defining a first obtuse angle, the first shaft having a first shaft length; and (d) a second shaft connected to the first shaft on said proximal end. The catheter is flexible so as to afford being straightened when it is advanced over a guide wire. The catheter resiliently returns to a multi-angulated position after the guide wire is withdrawn.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "radial ventriculography" refers to cardiac procedure wherein a catheter is threaded through an arm of a patient rather than the larger femoral artery in the groin. For example, the catheter may be threaded through the small radial artery in the wrist, the ulnar artery in the wrist, the brachial artery in the elbow, or any other peripheral arteries in the arm of a patient. The catheter is then advanced to the left ventricule of the patient and a radiopaque dye is then injected into the left ventricle. A visual representation is then made of the left ventricle.

2. Multi-Angulated Catheter

Figure 1:
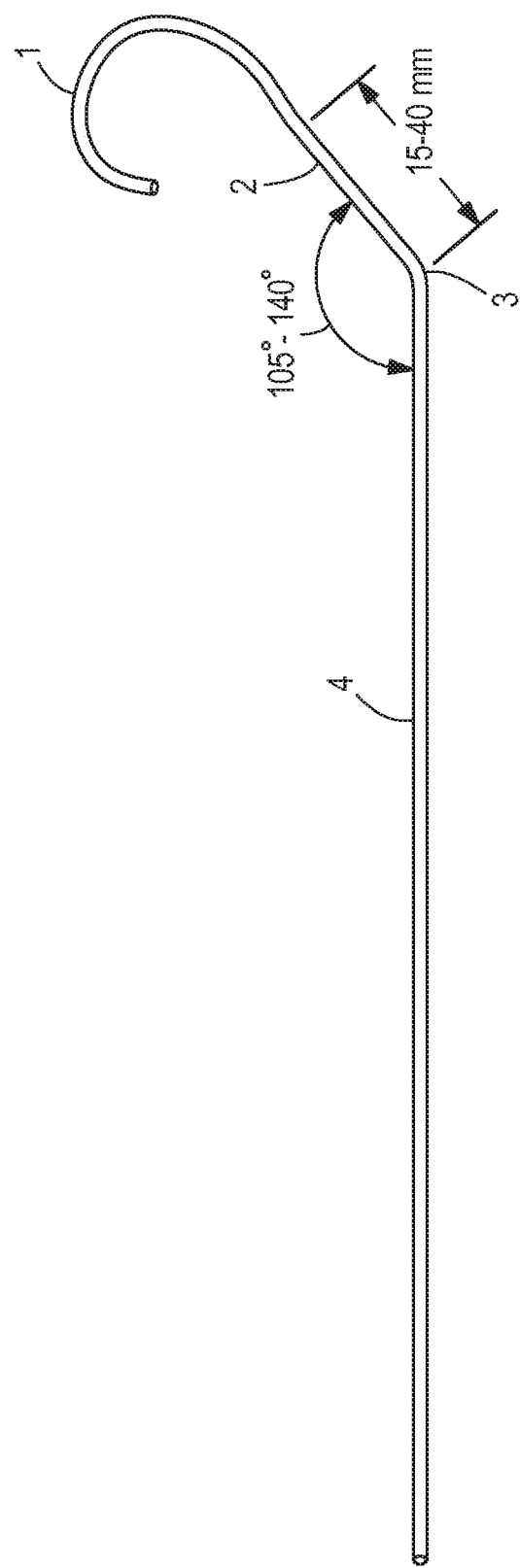
FIG. 1. Schematic illustration of a conventional catheter.

Turning now to the drawings, FIG. 1 shows a conventional catheter comprising in order: (a) a coiled end 1; (b) a first straight portion 2 having a length of about 15 to about 40 mm; (c) a first bend 3; and (d) a shaft 4, in which the first straight portion 2, the first bend 3 and the shaft 4 define an angle of about 105° to about 140°. The coiled end 1 of the catheter defines a spiral "pigtail." The tip of the pigtail comprises an open aperture and the pigtail may also contain one or more apertures to aid in uniform filling the ventricle with x-ray contrast fluid. Pigtail catheters are known in the art. See, for example U.S. Pat. No. 5,307,403, incorporated herein by reference. The catheter can be produced in any of the standard French sizes (4, 5, 6, 7 or 8 French).

Figure 2:
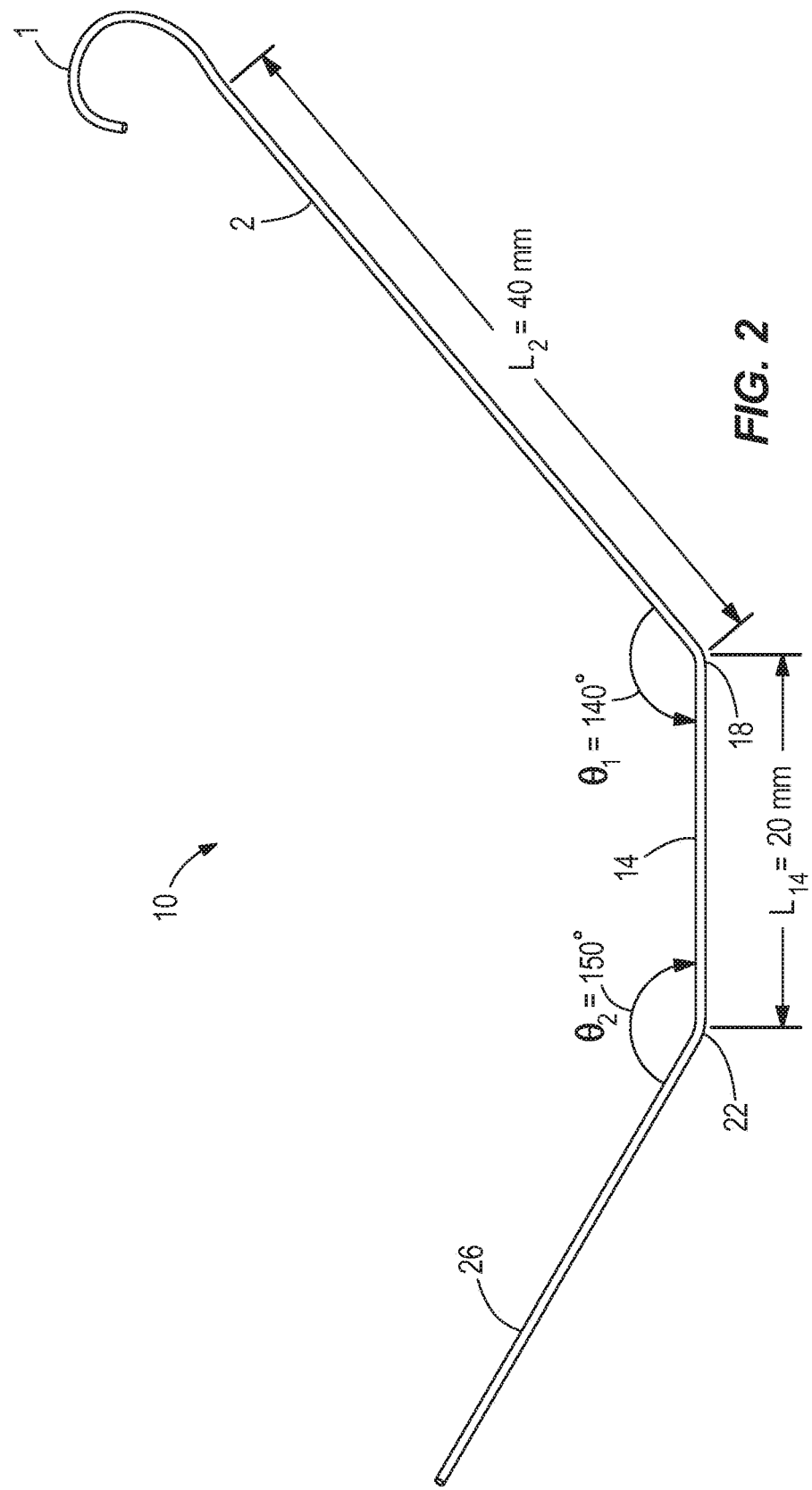
FIG. 2. Schematic illustration of a multi-angulated catheter according to one embodiment of the invention.
Figure 3:
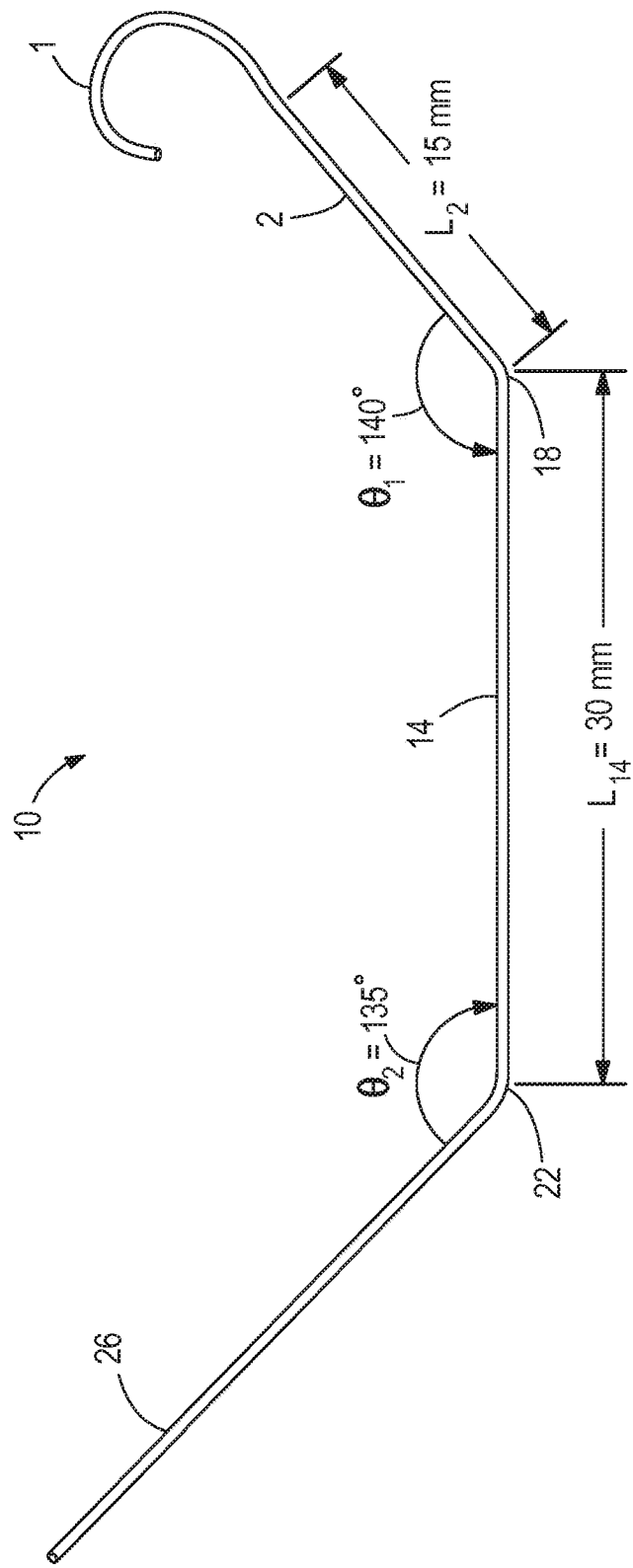
FIG. 3. Schematic illustration of the multi-angulated catheter of FIG. 2 with slightly different dimensions.

FIGS. 2 and 3 show a multi-angulated catheter 10 according to one embodiment of the invention, comprising, in order: (a) a coiled end 1; (b) a first straight portion 2 having a straight portion length $L_2$, (c) a first shaft 14 connected to said first straight portion 2 at a first obtuse angle $\theta_1$, wherein said first shaft 14 has a first shaft length $L_{14}$, the first shaft 14 including a distal end 18 connected to the first straight portion 2 and a proximal end 22 opposite said distal end 18, and (d) a second shaft 26 connected to the first shaft 14 on the proximal end 22. The first shaft 14 extends from the second shaft 26 at a second obtuse angle $\theta_2$. In the illustrated embodiment, the first obtuse angle $\theta_1$ is a positive angle, i.e., defined by a counterclockwise rotation when viewed from above, and the second obtuse angle $\theta_2$ is a negative angle, i.e., defined by a clockwise rotation when viewed from above. When viewed from below, however, the first obtuse angle $\theta_1$ is a negative angle and the second obtuse angle $\theta_2$ is a positive angle.

In an aspect, the first straight portion length $L_2$ is so dimensioned as to facilitate accessing a left ventricle from an arm of a patient. In some embodiments, the first straight portion length $L_2$ is about 15 mm to about 40 mm. For example, FIG. 2 illustrates the first straight portion length $L_2$ as 40 mm, and FIG. 3 illustrates the first straight portion length $L_2$ as 15 mm. In further embodiments, the first straight portion length is about 15 mm or more, about 16 mm or more, about 17 mm or more, about 18 mm or more, about 19 mm or more, about 20 mm or more, about 21 mm or more, about 22 mm or more, about 23 mm or more, about 24 mm or more, about 25 mm or more, about 26 mm or more, about 27 mm or more, about 28 mm or more, about 29 mm or more, about 30 mm or more, about 31 mm or more, about 32 mm or more, about 33 mm or more, about 34 mm or more, about 35 mm or more, about 36 mm or more, about 37 mm or more, about 38 mm or more, or about 39 mm or more. In further embodiments, the first straight portion length $L_2$ is about 40 mm or less, about 39 mm or less, about 38 mm or less, about 37 mm or less, about 36 mm or less, about 35 mm or less, about 34 mm or less, about 33 mm or less, about 32 mm or less, about 31 mm or less, about 30 mm or less, about 29 mm or less, about 28 mm or less, about 27 mm or less, about 26 mm or less, about 25 mm or less, about 24 mm or less, about 23 mm or less, about 22 mm or less, about 21 mm or less, about 20 mm or less, about 19 mm or less, about 18 mm or less, about 17 mm or less, or about 16 mm or less. This includes a first straight portion length $L_2$ of about 30 mm to about 40 mm.

In an aspect, the first shaft length $L_{14}$ is so dimensioned as to facilitate accessing a left ventricle from an arm of a patient. In some embodiments, the first shaft length $L_{14}$ is about 20 mm to about 40 mm. For example, FIG. 2 illustrates the first shaft length $L_{14}$ as 20 mm, and FIG. 3 illustrates the first shaft length $L_{14}$ as 30 mm. In further embodiments, the first shaft length $L_{14}$ is about 20 mm or more, about 21 mm or more, about 22 mm or more, about 23 mm or more, about 24 mm or more, about 25 mm or more, about 26 mm or more, about 27 mm or more, about 28 mm or more, about 29 mm or more, about 30 mm or more, about 31 mm or more, about 32 mm or more, about 33 mm or more, about 34 mm or more, about 35 mm or more, about 36 mm or more, about 37 mm or more, about 38 mm or more, or about 39 mm or more. In further embodiments, the first shaft length $L_{14}$ is about 40 mm or less, about 39 mm or less, about 38 mm or less, about 37 mm or less, about 36 mm or less, about 35 mm or less, about 34 mm or less, about 33 mm or less, about 32 mm or less, about 31 mm or less, about 30 mm or less, about 29 mm or less, about 28 mm or less, about 27 mm or less, about 26 mm or less, about 25 mm or less, about 24 mm or less, about 23 mm or less, about 22 mm or less, or about 21 mm or less. The second shaft 26 has a second shaft length, and the second shaft length is greater than said first shaft length $L_{14}$.

In an aspect, the first and second obtuse angles $\theta_1$, $\theta_2$ are so dimensioned as to facilitate accessing a left ventricle from an arm of a patient. In the illustrated embodiments, the first obtuse angle $\theta_1$ is about 140°. In other embodiments, however, the first obtuse angle $\theta_1$ may be about 105° to about 140°. In further embodiments, the first obtuse angle $\theta_1$ is about 105° or more, about 110° or more, about 115° or more, about 120° or more, about 125° or more, about 130° or more, or about 135° or more. In further embodiments, the first obtuse angle $\theta_1$ is about 140° or less, about 135° or less, about 130° or less, about 125° or less, about 120° or less, about 115° or less, or about 110° or less. Furthermore, in some embodiments, the second obtuse angle $\theta_2$ is about 135° to about 150°. For example, FIG. 2 illustrates the second obtuse angle $\theta_2$ as 150°, and FIG. 3 illustrates the second obtuse angle $\theta_2$ as 135°. In some embodiments, the second obtuse angle $\theta_2$ is about 135° or more, about 140° or more, or about 145° or more. In further embodiments, the second obtuse angle $\theta_2$ is about 150° or less, about 145° or less, or about 140° or less.

In some embodiments, the proximal end 22 is positioned from the coiled end 1 at a distance of about 30 mm to about 60 mm. In some embodiments, the proximal end 22 is positioned from the coiled end 1 at a distance of about 30 mm or more, about 35 mm or more, about 40 mm or more, about 45 mm or more, about 50 mm or more, or about 55 mm or more. In further embodiments, the proximal end 22 is positioned from the coiled end 1 at a distance of about 60 mm or less, about 55 mm or less, about 50 mm or less, about 45 mm or less, about 40 mm or less, or about 35 mm or less.

The multi-angulated catheter 10 is flexible so as to afford being straightened when it is advanced over a guide wire. The multi-angulated catheter 10 resiliently returns to a multi-angulated position after the guide wire is withdrawn. The catheter according to this invention may be made of any physiologically-compatible material having sufficient pliability and elasticity to permit bending of the catheter with no resultant permanent deformation. Such materials are known in the art and include, for example plastics such as polyurethane. Additionally, the catheter may further comprise, on its surface or a portion thereof a friction reducing agent which may be a hydrophilic polymer. Such agent, when wetted, as takes places in the insertion of the catheter into the aorta, provide an improved slippery surface to the catheter, which greatly assists in its placement prior to applying aliquots of x-ray contrast media to the heart. In further embodiments, the catheter optionally comprises an inner lining of resin polymer that may be braided. The inner lining may help provide a suitable stiffness to the catheter.

Figure 4:
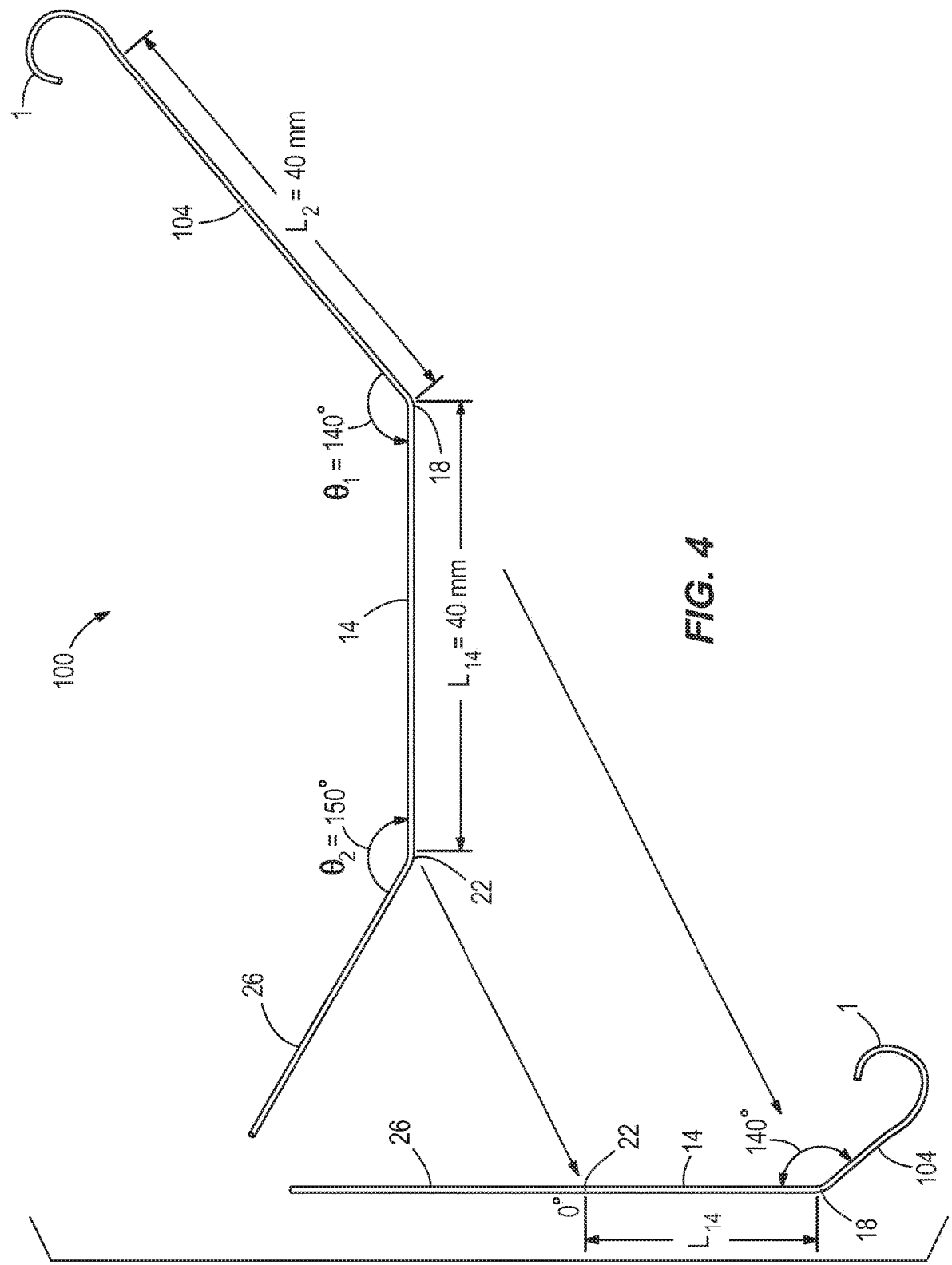
FIG. 4. Schematic illustration of a multi-angulated catheter according to an alternate embodiment of the invention.

FIG. 4 shows a multi-angulated catheter according to an alternate embodiment of the invention. Like parts are identified using like reference numerals. The multi-angulated catheter 100 in this embodiment comprises in order: (a) a coiled end 1; (b) a first straight portion 104 having a first straight portion length; (c) a first shaft 14 including a distal end 18 connected to the first straight portion 104 and a proximal end 22 opposite the distal end 18, the first shaft 14 having a first shaft length $L_{14}$; and (d) a second shaft 26 connected to the first shaft 14 on the proximal end 22. The multi-angulated catheter 100 is flexible so as to afford being straightened when it is advanced over a guide wire. The multi-angulated catheter 100 resiliently returns to a multi-angulated position after the guide wire is withdrawn. The first shaft 14 and the first straight portion 104 define a first obtuse angle $\theta_1$ when viewed from a direction substantially perpendicular to a plane defined by the first and second shafts 14, 26. The first straight portion 104 extends out of plane with respect to the plane defined by the first and second shafts 14, 26.

In some embodiments, the first straight portion 104 extends from the plane defined by the first and second shafts 14, 26 at an angle of about 5° to about 140°. In some embodiments, the first straight portion 104 extends from the plane defined by the first and second shafts 14, 26 at an angle of about 5° or more, about 10° or more, about 15° or more, about 20° or more, about 25° or more, about 30° or more, about 35° or more, about 40° or more, about 45° or more, about 50° or more, about 55° or more, about 60° or more, about 65° or more, about 70° or more, about 75° or more, about 80° or more, about 85° or more, about 90° or more, about 95° or more, about 100° or more, about 105° or more, about 110° or more, about 115° or more, about 120° or more, about 125° or more, about 130° or more, or about 135° or more. In further embodiments, the first straight portion 104 extends from the plane defined by the first and second shafts 14, 26 at an angle of about 140° or less, about 135° or less, about 130° or less, about 125° or less, about 120° or less, about 115° or less, about 110° or less, about 105° or less, about 100° or less, about 95° or less, about 90° or less, about 85° or less, about 80° or less, about 75° or less, about 70° or less, about 65° or less, about 60° or less, about 55° or less, about 50° or less, about 45° or less, about 40° or less, about 35° or less, about 30° or less, about 25° or less, about 20° or less, about 15° or less, or about 10° or less. The first straight portion 104 in this embodiment creates a three-dimensional profile for the multi-angulated catheter 100. The three-dimensional profile of the multi-angulated catheter 100 can facilitate accessing a left ventricle from an arm of a patient.

3. Method of Using the Multi-Angulated Catheter

The present disclosure is also directed to a method of using the multi-angulated catheter. In an operation such as in a radial ventriculography, a physician inserts a guide wire into an arm of a patient. The guide wire may be a conventional J-tip wire with a diameter of 0.89 mm or 0.97 mm. The multi-angulated catheter 10, 100 is then inserted over the guide wire into the arm and advanced over the guide wire through an artery into the patient's heart. The multi-angulated catheter 10, 100 is flexible so as to afford being straightened when it is advanced over the guide wire. In some embodiments, the multi-angulated catheter 10, 100 is advanced through the axillary artery, the subclavian artery, the innominate artery, and the ascending aorta. The guide wire is then withdrawn, whereupon the multi-angulated catheter 10, 100 resiliently returns to a multi-angulated position.

The multi-angulated catheter 10, 100 is then advanced in the multi-angulated position into a left ventricle of the patient. In some embodiments, the multi-angulated catheter is advanced in a clockwise fashion into the left coronary cusp, which may cause the multi-angulated catheter 10, 100 to curl upwards. In the upwardly curled position, the multi-angulated catheter 10, 100 may be withdrawn slightly and rotated slightly counterclockwise, so as to allow it to prolapse in the left ventricular cavity.

A radiopaque dye is then injected into the left ventricle, and a visual representation is made of the left ventricle. In some embodiments, the position of the multi-angulated catheter 10, 100 may be adjusted before or during the dye injection and visual representation. For example, the position of the multi-angulated catheter 10, 100 may be adjusted with slight advancements such as forward and backward, and/or clockwise and counterclockwise, to find a central ventricular position. Such adjustments may help avoiding myocardial staining and ventricular ectopy, and may also help achieving full cavity opacification. In some embodiments, pressure measurements may be obtained when the multi-angulated catheter 10, 100 is positioned in the aorta or in the ventricle.

After the ventriculography is performed, the multi-angulated catheter 10, 100 is withdrawn into the ascending aorta.

The guide wire is then inserted to straighten the multi-angulated catheter 10, 100, and the catheter 10, 100 is then removed from the patient over the guide wire.

The foregoing has been provided for illustrative purposes only and is not intended to limit the scope of the invention as set forth in the claims.

The invention claimed is:

1. A multi-angulated catheter comprising, in order:
   (a) a coiled end;
   (b) a first straight portion having a first straight portion length;
   (c) a first shaft including a distal end connected to said first straight portion and a proximal end opposite said distal end, said first shaft having a first shaft length; and
   (d) a second shaft connected to said first shaft on said proximal end,
   wherein in a first viewing plane of the multi-angulated catheter in a first state, said first shaft is disposed at a first obtuse angle with respect to the first straight portion and said second shaft is disposed at a second obtuse angle with respect to the first shaft,
   wherein in a second viewing plane of the multi-angulated catheter in the first state, said first shaft and said second shaft define a plane such that an angle between the first shaft and the second shaft is 0 degrees,
   wherein in the second viewing plane of the multi-angulated catheter in the first state, said first straight portion extends out of the plane defined by said first and second shaft, and
   wherein the first viewing plane is perpendicular to the second viewing plane,
   wherein the first state of multi-angulated catheter is a multi-angulated position,
   wherein, when a guidewire is inserted through the multi-angulated catheter, the multi-angulated catheter is straightened, and
   wherein when the guidewire is removed, the multi-angulated catheter resiliently returns to the first state.

2. The multi-angulated catheter of claim 1, wherein said first straight portion extends from said plane at an angle of 5° to 140°.

3. The multi-angulated catheter of claim 1, wherein said first straight portion length is 15 mm to 40 mm.

4. The multi-angulated catheter of claim 1, wherein said first shaft length is 20 mm to 40 mm.

5. The multi-angulated catheter of claim 1, wherein said first obtuse angle is 105° to 140°.

6. The multi-angulated catheter of claim 1, wherein said second obtuse angle is 135° to 150°.

7. The multi-angulated catheter of claim 1, wherein said proximal end is positioned from said coiled end at a distance of 30 mm to 60 mm.

8. The multi-angulated catheter of claim 1, wherein said second shaft has a second shaft length, and said second shaft length is greater than said first shaft length.

9. The multi-angulated catheter of claim 1, wherein said first straight portion length, said first shaft length, and said first obtuse angle are so dimensioned as to facilitate accessing a left ventricle from an arm of a patient.

10. A multi-angulated catheter, comprising:
    a first straight portion adjacent a distal end of the multi-angulated catheter;
    a first shaft extending from a proximal end of the first straight portion; and
    a second shaft extending from a proximal end of the first shaft,
    wherein in a first viewing plane of the multi-angulated catheter in a first state, the first shaft is disposed at a first obtuse angle with respect to the first straight portion and the second shaft is disposed at a second obtuse angle with respect to the first shaft,
    wherein in a second viewing plane of the multi-angulated catheter in the first state, the first shaft and the second shaft define a plane such that an angle between the first shaft and the second shaft is 0 degrees,
    wherein in the second viewing plane of the multi-angulated catheter in the first state, the first straight portion extends out of the plane defined by the first and second shafts,
    wherein the first viewing plane is perpendicular to the second viewing plane,
    wherein the first state of multi-angulated catheter is a multi-angulated position,
    wherein, when a guidewire is inserted through the multi-angulated catheter, the multi-angulated catheter is straightened, and
    wherein when the guidewire is removed, the multi-angulated catheter resiliently returns to the first state.

11. The multi-angulated catheter of claim 10, wherein one of the first and second obtuse angles is a positive angle and the other is a negative angle.

12. The multi-angulated catheter of claim 10, wherein the first straight portion, the first shaft, and the second shaft form a generally concave shape.

13. The multi-angulated catheter of claim 10, further comprising a coiled end extending from a distal end of the first straight portion.

14. The multi-angulated catheter of claim 10, wherein the first obtuse angle is 105° to 140°.

15. The multi-angulated catheter of claim 10, wherein the second obtuse angle is 135° to 150°.

16. The multi-angulated catheter of claim 10, wherein the second shaft is longer than the first shaft.

17. The multi-angulated catheter of claim 10, wherein the total length of the first straight portion and first shaft is between 30 mm and 60 mm.

18. The multi-angulated catheter of claim 10, wherein the first straight portion extends out of the plane at an angle between 5° and 140°.

* * * * *

UNITED STATES PATENT AND TRADEMARK OFFICE
CERTIFICATE OF CORRECTION

| | |
|---|---|
| PATENT NO. | : 11,583,626 B2 |
| APPLICATION NO. | : 16/673186 |
| DATED | : February 21, 2023 |
| INVENTOR(S) | : Mladen I. Vidovich |

It is certified that error appears in the above-identified patent and that said Letters Patent is hereby corrected as shown below:

In the Claims

Column 7, Line 29, Claim 1 reads, "... defined by said first and second shaft..." which should read, "... defined by said first and second shafts..."

Signed and Sealed this
Eighteenth Day of April, 2023

Katherine Kelly Vidal
*Director of the United States Patent and Trademark Office*